United States Patent [19]
Pek et al.

[11] Patent Number: 5,324,516
[45] Date of Patent: Jun. 28, 1994

[54] GALENIC COMPOSITION FOR DECREASING BLOOD ALCOHOL CONCENTRATION

[75] Inventors: Un H. Pek; Moon H. Kim; Sung K. Hwang, all of Seoul; Chan K. Park, Kyonggi; Oh H. Kwon, Inchun, all of Rep. of Korea

[73] Assignees: Doosan Technical Center; Doosan Industrial Company, both of Rep. of Korea

[21] Appl. No.: 975,168

[22] Filed: Nov. 16, 1992

[30] Foreign Application Priority Data

Dec. 19, 1991 [KR] Rep. of Korea ............... 91-23406

[51] Int. Cl.$^5$ ............................................. A61K 35/78
[52] U.S. Cl. .................................. 424/195.1; 514/23; 514/811
[58] Field of Search .................... 424/195.1, ; 514/23, 514/811

[56] References Cited

U.S. PATENT DOCUMENTS 5,204,369  4/1993  Vallee et al. ..................... 514/456

OTHER PUBLICATIONS

Sakai "Effect of Water Extracts of Aloe and some Herbs in decreasing Blood Ethanol concentration in Rats", Chem. Pharm. Bull 37(1)155-159, Jan. 1989.
Mascord et al. "The Effect of Fructose on Alcohol Metabolism and on the [Lactate]/[Pyruvate] Ratio in Man", Alcohol and Alcoholism vol. 26, No. 1, pp. 53-59, 1991.
Tygstrup "The Mechanism of the Fructose Effect on the Ethanol Metabolism of the Human Liver", Journal of Clinical Investigation, vol. 44, No. 5, 1965, pp. 817-829.
Ylikahri "Effects of Fructose and Glucose on Ethanol-Induced Metabolic Changes and on the Intensity of Alcohol Intoxication and Hangover", Europ. J. Clin. Invest, 6, pp. 90-102, 1976.
Sakai "Effect of water Extracts of Crude Drugs in Decreasing blood Ethanol Concentrations in Rats" Chem. Pharm. Bull, 35, 1987, pp. 4597-4604.
Brown et al "A Controlled Trial of Fructose in the Treatment of Acute Alcoholic Intoxication" The Lancet, Oct. 28, 1972, pp. 898-900.
Chemical Abstracts 114 (26): 254021k, 1990.
Goodman Gilman et al. (Editors), *The Pharmacological Basis of Therapeutics*, (6th Edition), New York, Macmillan, 1980, pp. 551-553.

*Primary Examiner*—Marianne M. Cintins
*Assistant Examiner*—M. Moezie
*Attorney, Agent, or Firm*—Lowe, Price, LeBlanc & Becker

[57] ABSTRACT

The galenic composition of this invention has been found to possess valuable pharmacological properties in the prevention of the aftereffects related to ingesting excessive amounts of ethanol. The inventive composition decreases blood alcohol concentration and reduces the increased content of neutral fat in the blood due to alcohol intake. The composition comprises an amount of fructose and an aqueous extract of pueraria flower, phaseoli radiati semen and pinelliae tuber sufficient to increase, in vivo, metabolic activity of alcohol dehydrogenase and aldehyde dehydrogenase enzymes and a pharmaceutically acceptable carrier, adjuvant or excipient therefor. A method of treating the aftereffects of ingesting excessive amounts of ethanol is also disclosed.

13 Claims, No Drawings

GALENIC COMPOSITION FOR DECREASING BLOOD ALCOHOL CONCENTRATION

BACKGROUND OF INVENTION

1. Field of the Invention

The present invention relates to a galenic composition, useful for alleviating the aftereffects due to an excessive intake of ethanol, commonly referred to as alcohol. More particularly, the present invention is concerned with such treatment using pueraria flower, phaseoli radiati semen, pinelliae tuber and fructose as the primary components of the galenic composition and administering such composition prior to ingesting ethanol.

2. Information Disclosure Statement

The consumption of alcohol is rapidly increasing as modern economic circumstances improve and leisure time increases. After drinking, alcohol is rapidly absorbed from the gastro-intestinal tract and distributed uniformly in the body. The absorbed alcohol is mainly, i.e. about 90% metabolized in the liver. Excess alcohol can induce various toxic effects in the human body. Short term toxic effects include confused consciousness, ataxia, headache, vomiting, facial flushing, tachycardia, palpitation, and the like. Long term effects from a history of excessive alcohol use include cirrhosis, alcohol liver disease, neurologic, gastrointestinal and others known to the medical practitioner. The present invention is directed to short term toxic effects.

Today these undesirable effects are treated by utilizing a synthetic medicine or a popular remedy based on certain crude drugs or on foodstuffs. Although the use of synthetic medicine can alleviate the aftereffects of drinking alcohol, they may themselves cause undesirable side effects.

The popular remedy which may be most typically mentioned includes ginseng extract/honey combination, fresh juice of pueraria root and the like. Such popular remedies show no side effects but are hard to utilize since the crude drugs or foodstuffs should be made each time the remedy is needed.

The present inventors have extensively investigated the compositions which can help hangover, based on the popular remedy, especially the composition utilizing crude drugs, which can conveniently alleviate the aftereffects of excessive alcohol intake without manifesting side effects.

The effectiveness and safety of crude drugs have been recognized only from long experience. However, in practice, only some crude drugs have been scientifically recognized in the efficacy. Recently, since serious problems caused by side effects and resistance of various synthetic medicines have been raised, the development of medicines, having no side effects, based on natural substances, especially herb medicines has been strongly required. Thus, the study on the efficacy and active ingredient of important crude drug has been actively under way at home and abroad.

The present inventors have extensively searched for herb medicines useful for removing alcohol toxicity through animal experiments and have analyzed the biochemical changes obtained from the administration of a galenic composition containing certain herb medicines in animal and human being to identify that this galenic composition can greatly reduce the alcohol level in the blood. Now, the present invention has been completed on the basis of this experimental result.

Therefore, it is an object of the present invention to decrease blood concentration of alcohol by providing a composition comprising an amount of fructose and an aqueous extract of pueraria flower, phaseoli radiati semen and pinelliae tuber sufficient to increase, in vivo, metabolic activity of alcohol dehydrogenase (ADH) and aldehyde dehydrogenase (ALDH) enzymes and a pharmaceutically acceptable carrier, adjuvant or excipient therefor.

It is a further object of the present invention to provide a composition which can be easily administered prior to ingesting ethanol.

It is a further object of the present invention to provide a method which treats, i.e. alleviates, or at least attenuates, the short term aftereffects of drinking ethanol.

It is a further object of the present invention to provide a composition which when orally administered to a person who expects to ingest ethanol in about thirty minutes, increases the metabolic activity of alcohol dehydrogenase (ADH) and aldehyde dehydrogenase (ALDH) enzymes in the liver of such person such that the short term aftereffects of ethanol are treated, i.e., alleviated, or at least attenuated.

It is a further object of the present invention to provide a method for decreasing blood ethanol concentration comprising administering to a mammal prior to ethanol ingestion an amount of a composition comprising fructose and an aqueous extract of pueraria flower, phaseoli rediati semen and pinelliae tuber sufficient to increase the metabolic activity of alcohol dehydrogenase (ADH) and aldehyde dehydrogenase (ALDH) enzymes in the liver of the mammal administered said composition prior to ingesting alcohol.

The preceding objects should be construed as merely presenting a few of the more pertinent features and applications. of the invention. Many other beneficial results can be obtained by applying the disclosed invention in a different manner or modifying the invention within the scope of the disclosure. Accordingly, other objects and a fuller understanding of the invention may be had by referring to both the Summary of the Invention and the Detailed Description, below, which describe the preferred embodiment in addition to the scope of the invention defined by the claims considered in conjunction with the accompanying tables and tests.

SUMMARY OF THE INVENTION

The galenic composition for decreasing blood alcohol concentration is defined by the claims with a specific embodiment shown in the examples and tables. For the purpose of summarizing the invention, the invention relates to a galenic composition comprising an amount of fructose and an aqueous extract of pueraria flower, phaseoli radiati semen and pinelliae tuber sufficient to increase, in vivo, metabolic activity of alcohol dehydrogenase and aldehyde dehydrogenase enzymes and a pharmaceutically acceptable carrier, adjuvant or excipient therefor. The primary composition includes fructose, pueraria flower, phaseoli radiati semen and pinelliae tuber as the core components which must be present in any composition according to the present invention. Preferably, the pueraria flower, the phaseoli radiati semen, the pinelliae tuber and fructose are present in the composition in a relative dry weight ratio of 0.2–1:0.2–1:0.2–1:0.2–1.

The primary galenic composition may further include one or more adjuvant components selected from the group consisting of: arthemisiae herba, alismatis rhizoma, gardeniae fructus, scutellariae radix, coptidis rhizoma, moutan cortex radicis, black soybean, ginseng radix, small red bean, puerariae radix, magnoliae cortex, aurantii nobilis pericarpium, amomi semen, crataegi fructus, arecae semen, massa medicata fermentata, malt, amomi fructus and glycyrrhizae radix. Preferably, when the galenic composition includes pueraria flower, phaseoli radiati semen, pinelliae tuber and fructose, i.e. the primary composition, together with the adjuvant component(s), as described above, the relative weight relationship of the primary composition to the adjuvant component(s) is expressed as a ratio of 1:0.1–1:1 by dry weight.

The galenic composition according to the present invention may further include one or more sweetening agents selected from the group consisting of: dextrose, saccharin, sodium saccharin, sorbitol, white sugar, sugar, lactose, honey, glucose, aspartame and mannitol. Also, the galenic composition according to the present invention may further include one or more flavoring agents selected from the group consisting of: peppermint, spearmint and menthol.

The preferred route of administration is the oral route administration.

A galenic composition for decreasing blood alcohol concentration and which includes the primary composition along with certain adjuvant components is composed of 10 grams of fructose in an aqueous filtered extract of about 7.5 grams of pueraria flower, 7.5 grams of phaseoli radiati semen, 4.5 grams of pinelliae tuber, 3.75 grams of arthemisiae herba, 3.75 grams of gardeniae fructus, 3.75 grams of scutellariae radix, 3.75 grams of coptidis rhizoma, 3.75 grams of black soybean, 3.75 grams of puerariae radix, 3.75 grams of aurantii nobilis pericarpium, 3.75 grams of glycyrrhizae radix and 3.75 grams of ginseng radix to increase metabolic activity of alcohol dehydrogenase and aldehyde dehydrogenase enzymes and a pharmaceutically acceptable carrier, adjuvant or excipient therefor.

Another embodiment of the present invention is a method for decreasing blood ethanol concentration. The method comprises administering to a person prior to ethanol ingestion an amount of a composition comprising fructose and an aqueous extract of pueraria flower, phaseoli radiati semen and pinelliae tuber sufficient to increase the metabolic activity of alcohol dehydrogenase and aldehyde dehydrogenase enzymes in the liver of the person administered the composition prior to ingesting alcohol. The composition is preferably administered to the person about 30 minutes prior to the ingestion of ethanol and most preferably orally administered 30 minutes prior to ingesting alcohol.

Another embodiment of the present invention includes a method of treating alcoholic aftereffects in a mammal about to ingest excessive alcohol by administering prior to alcoholic ingestion an amount of a composition comprising fructose and an aqueous extract of pueraria flower, phaseoli radiati semen and pinelliae tuber sufficient to increase the metabolic activity of alcohol dehydrogenase and aldehyde dehydrogenase enzymes in the liver of the mammal administered the composition prior to ingesting alcohol. Preferably, the composition is orally administered.

The composition of this invention may be administered to mammals, especially humans.

The pharmacologically active composition of this invention can be processed in accordance with the conventional methods practiced in pharmacy to produce medicinal agents for administration to mammal patients, and especially humans.

For oral administration, while liquid extracts and powders are exemplified below, other oral dosage forms which are also suitable are tablets, dragees, liquids, drops or capsules. A syrup, elixir, or the like, can be used where a sweetened vehicle is employed.

As can be appreciated by those skilled in the art, it is not known whether the present composition and method have an influence on long term or chronic alcohol aftereffects as no testing for this has been undertaken. Thus, the purpose of the present composition and method is to treat, i.e., alleviate or attenuate, the unpleasant short term aftereffects of drinking too much alcohol, commonly known as a "hangover". As to what is considered "excessive" is within the knowledge of one who has enjoyed alcoholic beverages in the past and is considered somewhat dependent on the person.

The more pertinent and important features of the present invention have been outlined above in order that the detailed description of the invention which follows will be better understood and that the present contribution to the art can be fully appreciated. Additional features of the invention described hereinafter form the subject of the claims of the invention. Those skilled in the art can appreciate that the conception and the specific embodiment disclosed herein may be readily utilized as a basis for modifying or designing other structures for carrying out the same purposes of the present invention. Further, those skilled in the art can realize that such equivalent constructions do not depart from the spirit and scope of the invention as set forth in the claims.

DETAILED DESCRIPTION OF THE INVENTION

The present invention is to provide a galenic composition, i.e. a medicinal composition prepared by extracting active constituents from plants, for alleviating the aftereffects caused by excessive alcohol intake and which contains pueraria flower, phaseoli radiati semen, pinelliae tuber and fructose as the primary ingredients.

The galenic composition of the present invention stimulates alcohol metabolism with alcohol metabolizing enzymes (alcohol dehydrogenase, aldehyde dehydrogenase) in the liver after alcohol intake to thereby reduce the level of alcohol in the blood at a faster rate than without administering the composition of the present invention and, therefore, reduces the toxic effects of alcohol.

In addition, the galenic composition of the present invention reduces the increased content of neutral fat in the blood due to alcohol intake, as well as the alcohol level in the blood.

The galenic composition of the present invention contains as the primary ingredients pueraria flower, phaseoli radiati semen, pinelliae tuber and fructose. The galenic composition of the present invention can alleviate all the symptoms associated to the aftereffects of excessive drinking by increasing the activity of the enzymes responsible for alcohol metabolism, i.e. alcohol dehydrogenase (ADH) and aldehyde dehydrogenase , (ALDH) to stimulate alcohol metabolism.

Pueraria flower is the bud of Pueraria thunbergiana Bentham belonging to Leguminosae. The pueraria flower used in the present invention is a flower which is in bud prior to blooming, which has a pale purple color, and should not contain any flower stalks or other associated foreign substances. Pueraria flower has been used in removing alcohol toxic effects and in alleviating thirst and gastro-intestinal irritation.

Phaseoli radiati semen is the seed of Phaseolus radiatus Linne belonging to Leguminosae. In the present invention, the uniform and baird seed having a green-yellow color should be used. Phaseoli radiati semen has been used mainly for its antipyretic, detoxicating and diuretic effects.

Pinelliae tuber is a crude herb medicine obtained by drying the tuber cortex of Pinellia ternata Breitenbach belonging to Araceae, which has been known as having antiemetic and expectorant activities.

Fructose is a monosaccharide ($C_6H_{12}O_6$) which is used for energy supply in diabetes and diabetes related conditions and detoxication in acute alcohol intoxication.

These ingredients are present in the composition of the present invention in a dry weight ratio of 0.2-1:0.2-1:0.2-1:0.2-1, pueraria flower: phaseoli radiati semen: pinelliae tuber: fructose.

The galenic composition of the present invention can additionally contain adjuvant herb medicinal ingredients and auxiliary components such as sweeteners, flavoring agents, and the like. That is, conventional excipients, i.e. pharmaceutically acceptable organic or inorganic carrier substances suitable for oral administration which do not deleteriously react with or on the active components. Suitable pharmaceutically acceptable carriers include but are not limited to water, salt solutions, alcohols, gum arabic, vegetable oils, benzyl alcohols, gelatine, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose and the like.

The adjuvant herb medicine, which can be contained in the galenic composition of the present invention, is a substance capable of increasing the alcohol metabolism-stimulating effect due to the main ingredients. The adjuvant medicine is one or more substances selected from the group consisting of arthemisiae herba, alismatis rhizoma, gardeniae fructus, scutellariae radix, coptidis rhizoma, moutan cortex radicis, black soybean, ginseng radix, small red bean, puerariae radix, magnoliae cortex, aurantii nobilis pericarpium, amomi semen, crataegi fructus, arecae semen, massa medicata fermentata, malt, amomi fructus and glycyrrhizae radix. The preferred adjuvant medicines are arthemisiae herba, gardeniae fructus, scutellariae radix, coptidis rhizoma, black soybean, ginseng radix, puerariae radix, aurantii nobilis pericarpium and glycyrrhizae radix.

Such adjuvant herb medicinal ingredients can be added in the weight ratio of 1:0.1 to 1: 1 with respect to the main ingredients.

The present composition can also include a sweetening agent and a flavoring agent, if necessary. For this purpose, one or more sweetening agents selected from the group consisting of dextrose, saccharin, sodium saccharin, sorbitol, white sugar, sugar, lactose, honey, glucose and mannitol can be suitably added.

Flavoring agents include one or more substances selected from peppermint, spearmint, menthol and other flavoring agents which are harmless to the human body can be used.

Although the composition of the present invention may be used as it is, it can be formulated into various forms, such as liquid formulations, especially a water extract or suspension, pills, tablets, capsules, powders or soft extract for easy oral administration. Such formulations can be manufactured by means of conventional methods known in the pharmaceutically technical field.

The composition of the present invention may be orally administered in an amount such that 1.5 to 7.5 grams of pueraria flower, 1.5 to 7.5 grams of phaseoli radiati semen, 1.5 to 7.5 grams of pinelliae tuber and 3 to 15 grams of fructose are administered at one time.

Preferably, a single dose comprising 5.25 grams of fructose and the aqueous extract of 3.75 grams of pueraria flower, 3.75 grams of phaseoli radiati semen and 1.875 grams of pinelliae tuber is administered.

When the composition is in the form of a lyophylized powder, the single amount of the composition is preferably 10 to 15 g.

The present invention is more thoroughly explained through the following preparation examples and tests.

EXAMPLE 1

150 grams of pueraria flower, 150 grams of phaseoli radiati semen and 75 grams of pinelliae tuber are finely chopped and then extracted with 4 liters of water at 80 to 100 degrees Centigrade for 2 to 3 hours. The extract is filtered and 140 grams of fructose and the suitable amount of purified water are added to the filtrate to prepare the desired preparation according to the present invention.

EXAMPLE 2

150 grams of pueraria flower, 150 grams of phaseoli radiati semen and 75 grams of pinelliae tuber, 150 grams of puerariae radix, 75 grams of scutellariae radix, 75 grams of arthemisiae herba, 75 grams of gardeniae fructus and 75 grams of glycyrrhizae radix are finely chopped and then extracted with 8 liters of water at 80 to 100 degrees Centigrade for 2 to 3 hours. To the extract is added 150 grams of fructose to prepare the desired preparation according to the present invention.

The resulting extraction composition is an amount sufficient for a single dose in 20 adult persons.

EXAMPLE 3

7.5 grams of pueraria flower, 7.5 grams of phaseoli radiati semen and 3.75 grams of pinelliae tuber are finely chopped and then extracted with 150 ml of water at 80 to 100 degrees Centigrade for 2.5 hours, filtered and 7 grams of fructose are added to the filtrate to prepare the desired galenic composition.

The resulting extraction composition is an amount sufficient for a single dose in an adult male or female.

EXAMPLE 4

7.5 grams of pueraria flower, 7.5 grams of phaseoli radiati semen and 4.5 grams of pinelliae tuber, 3.75 grams of arthemisiae herba, 3.75 grams of gardeniae fructus, 3.75 grams of scutellariae radix, 3.75 grams of coptidis rhizoma, 3.75 grams of black soybean, 3.75 grams of puerariae radix, 3.75 grams of aurantii nobilis pericarpium, 3.75 grams of glycyrrhizae radix and 3.75 grams of ginseng radix are finely chopped and then extracted with 540 ml of water at 90 degrees Centigrade for 3 hours. The resulting aqueous extract is filtered. To the filtrate is added 10 grams of fructose and an appropriate amount of water is added, and the entire mixture is mixed to produce a homogeneous mixture, the desired galenic composition.

The resulting homogeneous mixture is the amount sufficient for a single dose in an adult human male or female.

EXAMPLE 5

15 grams of pueraria flower, 15 grams of phaseoli radiati semen, 6 grams of pinelliae tuber, 7.5 grams of arthemisiae herba, 7.5 grams of gardeniae fructus, 7.5 grams of scutellariae radix, 7.5 grams of coptidis rhizoma, 7.5 grams of black soybean, 7.5 grams of puerariae radix, 7.5 grams of aurantii nobilis spericarpium, 7,5 grams of glycyrrhizae radix, 7.5 grams of ginseng radix, 7.5 grams of small red bean, 7.5 grams of magnoliae cortex, 7.5 grams of amomi semen and 7.5 grams of amomi fructus are finely chopped and then extracted with 1.4 liter of fructose at 100 degrees Centigrade for 2.5 hours. The obtained extract is filtered. To the filtrate are added 14 grams of water and the appropriate amount of purified water and then mixed uniformly to prepare the desired galenic composition.

The galenic compositions listed in the following Table 1 can also be prepared according to the method analogous to the methods described in Examples 1 to 5.

TEST EXAMPLES

Test 1

Effect of the galenic composition on blood alcohol concentration in rats

The galenic composition manufactured in Example 1 is dried in a lyophilizer to obtain a powder which is then used as the test sample.

Male rats weighing 150 to 200 g are fasted for 18 to 24 hours and then divided into two groups, i.e. the control group and the test group, each of which consists of 10 rats. The test group is orally administered the galenic composition of the present invention prepared by dissolving 2 g of the test sample in the appropriate amount of water, per kg of body weight and the control group is given the same volume of water. After 30 minutes to one hour from the administration of the sample, 3 g of alcohol per kg of body weight is administered per oral to each of the control and test groups.

Blood is collected from the tail after 1, 2, 4 and 6 hours following alcohol administration. The collected blood is immediately treated to remove protein and then the alcohol concentration is determined.

The result of the assay for the change of alcohol concentration in blood over a period of time is shown in the following Table 2.

TABLE 1

| | Galenic Compositions | | | | | | |
|---|---|---|---|---|---|---|---|
| | Herb Medicinal Materials | | | | | Water | |
| | Main Ingredient (content g) | | | | | for extraction | Extraction Time |
| Example No. | A | B | C | D | Adjuvant Ingredient (content g) | (ml) | (hr) |
| 6 | 3.75 | 3.75 | 2.5 | 5.25 | E(1.9), G(2), H(1.9), T(2.1) | 230 ml | 2.5 |
| 7 | 5.2 | 4.5 | 3.8 | 8.2 | E(2.8), G(3.0), J(2.9), H(2.0), N(1.8), T(2.5), R(2.5) | 400 ml | 3 |
| 8 | 7.5 | 7.5 | 3.75 | 7 | — | 150 ml | 2.5 |
| 9 | 7 | 6 | 3.2 | 7 | H(3), J(3.2), K(3.2), M(3.5), T(3), G(3), R(2.5), O(2.5), L(2) | 500 ml | 3 |
| 10 | 6 | 5.3 | 3.5 | 9 | E(3.1), G(3.1), H(3.1), I(3.0), K(2.5), M(2.1), N(2.1), T(2.5) | 470 ml | 2.6 |
| 11 | 4.3 | 4.1 | 2.8 | 6.1 | G(2.0), J(2.0), O(2.1), P(2.3), R(2), T(2.5) | 300 ml | 3 |
| 12 | 4.0 | 4.0 | 2.8 | 5.7 | E(2.5), J(2.5), K(2.5), M(2.0), T(1.2), L(1.5), O(1.5), F(1.0) | 320 ml | 3 |
| 13 | 7.0 | 7.0 | 3.5 | 12 | E(3.0), H(3.5), K(3.0), M(3.5), N(3.0), F(2.1), Q(2.1), R(2.5), S(3) | 570 ml | 3 |

Note:
A *Pueraria flower*
B *Phaseoli radiati semen*
C *Pinelliae tuber*
D *Fructose*
E *Arthemisiae herba*
F *Alismatis rhizoma*
G *Gardeniae fructus*
H *Scutellariae radix*
I *Coptidis rhizoma*
J *Black soybean*
K *Ginseng radix*
L *Small red bean*
M *Puerariae radix*
N *Aurantii nobilis pericarpium*
O *Crataegi fructus*
P *Arecae semen*
Q *Massa medicata fermentata*
R *Malt*
S *Amomi fructus*
T *Glycyrrhizae radix*

TABLE 2

Change of blood alcohol concentration in rat

| | Alcohol concentration (g/l) | | | |
|---|---|---|---|---|
| | 1 hr. | 2 hr. | 4 hr. | 6 hr. |
| Control Group | 2.530 | 2.229 | 0.851 | 0.232 |
| Test Group | 1.493 | 1.418 | 0.395 | 0.217 |

From the above Table, it can be seen that the alcohol concentration in blood of the test group which is given the galenic composition of the present invention is significantly reduced over a period of time in comparison with the control group.

Therefore, the above data obtained from the present test demonstrate that the galenic composition of the present invention stimulates alcohol metabolism.

Test 2

Effect of popular remedies on blood ethanol concentration in rats after the administration of ethanol In order to prove the superior effect of the galenic composition of the present invention in comparison with the popular remedy, the effect of popular remedies on blood ethanol concentration has been examined. In this test,. fresh juice of puerariae radix and ginseng extract/honey combination are prepared as mentioned below and then used as popular remedies.

The fresh puerariae radix was chopped and squeezed to obtain the fresh juice. The fresh juice was administered to rats at a dose of 10 ml/kg body weight. The 7.5 g of ginseng radix was extracted with 100 ml of water at 100° C. for 2.5 hours. To the extract, 10 g of honey were added. The ginseng extract/honey combination was administered to rats at a dose of 10 ml/kg body weight.

Male rats weighing 150 to 200 g were fasted for 18 to 24 hours and then divided into 3 groups, i.e. the control group and two test groups, each of which consists of 10 rats. The test group is orally administered either the fresh juice of puerariae radix or ginseng extract/honey combination. The control group is given the same volume of water. At 30 minutes to one hour after the administration of the sample, 3 g of ethanol per kg of body weight is administered per oral to each of the control and test groups.

Blood was collected from the tail at 1, 2, 4 and 6 hours following the ethanol administration and immediately deproteinized. The ethanol concentration of the deproteinized blood was determined.

The result of the assay for the change of alcohol concentration in blood over a period of time is shown in Table 3.

TABLE 3

Change of blood ethanol concentration in rats

| | Alcohol concentration (g/l) | | | |
|---|---|---|---|---|
| | 1 hr | 2 hr | 4 hr | 6 hr |
| Control group | 2.530 | 2.229 | 0.851 | 0.232 |
| Puerariae radix | 1.974 | 1.840 | 0.836 | 0.424 |
| Ginseng extract/honey combination | 1.955 | 1.658 | 0.413 | 0.302 |

The table shows that both the juice of puerariae radix and the ginseng extract/honey combination significantly reduce the blood ethanol concentration compared with the control group. However, when comparing the result of the present test with the result of Test 1 (Table 2), it can be clearly seen that the galenic composition of the present invention reduces much more the blood ethanol concentration in comparison with the popular remedies. Accordingly, it can be concluded that the galenic composition of the present invention is more effective in helping aftereffects due to excessive ethanol intake than the popular remedy.

TEST 3

Effect of each of primary ingredients of the galenic composition on blood ethanol concentration in rats In order to prove the superior effect of the galenic composition having a unique combination of four primary ingredients, the effect of each of primary four ingredients, i.e. pueraria flower, phaseoli radiati semen, pinelliae tuber and fructose, on blood ethanol concentration has been examined in rats.

The 50 g of pueraria flower was finely chopped and extracted with 1l of water at 100° C. for 2.5 hours. The extract was filtered and lyophilized in a freeze dryer. The 10.7 g of the powder was obtained.

The phaseoli radiati semen and pinelliae tuber were extracted and lyophilized in the same manner as described for puerariae flos. The 14.6 g and 7 g of powder were obtained from phaseoli radiati semen and pinelliae tuber, respectively.

The powder of pueraria flower, phaseoli radiati semen, pinelliae tuber, and fructose were dissolved in an adquate volume of water and administered to rats fasted 18 to 24 hours at a dose of 0.28 g, 0.39 g, 0.09 g and 1.2 g/kg body weight, respectively. The rats were treated in the same manner as Test 2.

The results of the assay for the change of alcohol concentration in blood over a period of time is shown in the following Table 4.

TABLE 4

Change of blood ethanol concentration in rats

| | Alcohol concentration (g/l) | | | |
|---|---|---|---|---|
| | 1 hr | 2 hr | 4 hr | 6 hr |
| Control group | 2.530 | 2.229 | 0.851 | 0.232 |
| Pueraria flower | 2.015 | 1.867 | 0.839 | 0.527 |
| Phaseoli radiati semen | 2.208 | 1.788 | 0.729 | 0.252 |
| Pinelliae tuber | 2.523 | 2.302 | 0.768 | 0.146 |
| Fructose | 1.984 | 1.654 | 0.724 | 0.325 |

The table shows that 3 samples except pinelliae tuber are slightly effective in reducing blood ethanol concentration.

However, when comparing the result of the present test with the result of Test 1 (Table 2), it can be clearly seen that the galenic composition of the present invention significantly reduces the blood ethanol concentration in comparison with each primary ingredient. Thus, it can be concluded that the galenic composition of the present invention having a unique combination of primary four ingredients produces a superior synergistic effect in lowering blood ethanol concentration, which cannot be expected from the effects of each primary ingredient.

Test 4

Influence of the galenic composition on the content of neutral fat in serum

From the rats of Test 1, the serum is separated after 6 hours following administration of alcohol and the content of neutral fat in the serum is measured.

TABLE 5

| Content of neutral fat in serum | |
| --- | --- |
| | Neutral fat (mg/dl) |
| Control Group | 133.11 |
| Test Group | 63.82 |

From the above table, it can be seen that the content of serum neutral fat in the test group is greatly reduced in comparison to the control group. Therefore, this result suggests that the galenic composition of the present invention can control the abnormality of fat metabolism due to the ingestion of alcohol.

Test 5

Assay for the activity of alcohol-metabolizing enzymes in rat liver

Male rats weighing 150 to 200 g are fasted for 18 to 24 hours and then divided into the control group and the test group, each of which consists of 40 rats. The test group is orally administered a solution containing 2 g of powder, which is prepared by drying the galenic composition produced in Example 1 with a lyophilizer, dissolved in purified water per kg of body weight and the control group is given the same volume of water. After 30 minutes to one hour after administration of the test sample, 3 g of alcohol per kg of body weight is administered per oral to each of the control and test groups.

After 1, 2, 4 and 6 hours from the alcohol administration, ten rats from each group are sacrificed and the liver is removed from the rats and then washed with physiological saline solution. The washed liver is pulverized with a homogenizer and then subjected to the ultracentrifugation to obtain a cytoplasmic fraction and a mitochondrial fraction.

The activity of alcohol dehydrogenase (ADH) in the cytoplasmic fraction and the activity of aldehyde dehydrogenase (ALDH) in the mitochondrial fraction are determined.

The activities of ADH and ALDH in the rat liver over a period of time are shown as follows.

TABLE 6

| | Change of ADH activity in rat liver | | | |
| --- | --- | --- | --- | --- |
| | ADH activity (mU/mg of protein) | | | |
| | 1 hr. | 2 hr. | 4 hr. | 6 hr. |
| Control Group | 8.88 ± 1.39 | 8.57 ± 0.68 | 8.44 ± 1.31 | 7.55 ± 1.01 |
| Test Group | 8.70 ± 1.17 | 10.24 ± 1.19 | 11.01 ± 1.94 | 12.37 ± 1.68 |

TABLE 7

| | Change of ALDH activity in rat liver | | | |
| --- | --- | --- | --- | --- |
| | ALDH activity (mU/mg of protein) | | | |
| | 1 hr. | 2 hr. | 4 hr. | 6 hr. |
| Control Group | 16.51 ± 1.15 | 17.23 ± 2.74 | 13.89 ± 1.38 | 13.43 ± 1.73 |
| Test Group | 19.71 ± 2.88 | 23.9 ± 1.63 | 17.07 ± 2.12 | 15.93 ± 1.4 |

From the above Table 6 and Table 7, it can be seen that the administration of the sample of the galenic composition according to the present invention results in an increase of ADH and ALDH activities in the rat liver. Therefore, it is considered that the decrease of alcohol concentration in blood after administration of the present galenic composition as shown in the above Table 2 is caused by the stimulation of alcohol metabolism due to an increase of the activity of alcohol-metabolizing enzymes in the liver.

Test 6

Influence of the galenic composition on the alcohol concentration in blood of rat The extract prepared in Example 2 is dried with a lyophilizer to obtain a powder which is then used as the test sample. Male rats weighing 150 to 200 g are fasted for 18 to 24 hours and then divided into a control group and a test group, each of which consists of ten rats. The test group is given orally the solution of 4 g of the test sample dissolved in the appropriate amount of purified water per kg of body weight and the control group is given the same volume of water. 3 grams of alcohol per kg of body weight is administered per oral to each of the control and test groups after one hour from administration of the sample.

After 1, 2, 4 and 6 hours following alcohol administration, blood is collected from rat tail and treated to remove proteins. Then, the alcohol concentration in blood is measured.

The alcohol concentration in blood over a period of time is shown below.

TABLE 8

| | Change of alcohol concentration in blood | | | |
| --- | --- | --- | --- | --- |
| | Alcohol concentration (g/l) | | | |
| | 1 hr. | 2 hr. | 4 hr. | 6 hr. |
| Control Group | 2.522 | 2.013 | 1.051 | 0.201 |
| Test Group | 1.392 | 1.265 | 0.491 | 0.099 |

From Table 8, it can be seen that the galenic composition manufactured in Example 2 decreases the alcohol concentration in blood more than the galenic composition of Example 1 used in Test 1. This shows that the use of puerariae radix, scutellariae radix, arthemisiae herba, gardeniae fructus and glycyrrhizae radix as adjuvant herb medicines, in addition to four primary ingredients, slightly increases alcohol metabolism in comparison with the only primary four ingredients used alone.

Test 7

Assay for the change of alcohol concentration in human blood after administration of the galenic composition.

This is a human test in which two healthy men take part.

Each subject fasts from ten o'clock in the evening before the test to the morning of the test day and is allowed to drink water without restriction, as needed. On the morning of the test day, the subject is allowed to drink 1.8 g of alcohol per kg of body weight. After 30 minutes and at 1, 2, 4 and 6 hours, blood is collected and the alcohol concentration in the blood is measured.

After one week, the test sample prepared by adding the appropriate amount of water to the galenic composition of Example 3 to make 100 ml of the total volume is administered to the same subject 30 minutes before the alcohol administration. Blood is collected after 30 minutes and at 1, 2, 4 and 6 hours following the alcohol administration and the alcohol concentration in blood is measured.

TABLE 9

| Change in the alcohol concentration in human blood | | | | | |
|---|---|---|---|---|---|
| | Alcohol concentration (g/l) | | | | |
| | 30 min. | 1 hr. | 2 hr. | 4 hr. | 6 hr. |
| Subject A | | | | | |
| Alcohol | 0.615 | 0.689 | 0.491 | 0.375 | 0.175 |
| Alcohol + Sample | 0.504 | 0.454 | 0.225 | 0.037 | 0.010 |
| Subject B | | | | | |
| Alcohol | 1.833 | 1.895 | 1.691 | 1.342 | 0.929 |
| Alcohol + Sample | 1.680 | 1.597 | 1.119 | 0.622 | 0.372 |

Test 8

Acute Toxicity Test

The extract prepared in Example 1 is dried in a lyophilizer to obtain 160 grams of a powder which is then used as the test sample.

For every dose of the test sample, ten of each of male and female mice weighing 20 to 25 g are used. Each amount of sample is dissolved in a certain amount of purified water and administered orally to each mouse. Thereafter, the clinical symptoms and vital conditions of each mouse are observed for 7 days. After the test is completed, each mouse is anatomized to observe the condition by the mactography.

TABLE 10

| | Acute Toxicity in Mouse | | | | | | |
|---|---|---|---|---|---|---|---|
| | Sample Amount (g/kg of body weight) | | | | | | |
| | 0 | 1 | 2 | 4 | 6 | 7 | 8 |
| | NUMBER OF SURVIVAL | | | | | | |
| Female | | | | | | | |
| 1 Day | 10 | 10 | 10 | 10 | 10 | 10 | 10 |
| 2 Day | 10 | 10 | 10 | 10 | 10 | 10 | 10 |
| 3 Day | 10 | 10 | 10 | 10 | 10 | 10 | 10 |
| 4 Day | 10 | 10 | 10 | 10 | 10 | 10 | 10 |
| 5 Day | 10 | 10 | 10 | 10 | 10 | 10 | 10 |
| 6 Day | 10 | 10 | 10 | 10 | 10 | 10 | 10 |
| 7 Day | 10 | 10 | 10 | 10 | 10 | 10 | 10 |
| Lethality (%) | 0 | 0 | 0 | 0 | 0 | 0 | 0 |
| Male | | | | | | | |
| 1 Day | 10 | 10 | 10 | 10 | 10 | 10 | |
| 2 Day | 10 | 10 | 10 | 10 | 10 | 10 | |
| 3 Day | 10 | 10 | 10 | 10 | 10 | 10 | |
| 4 Day | 10 | 10 | 10 | 10 | 10 | 10 | |
| 5 Day | 10 | 10 | 10 | 10 | 10 | 10 | |
| 6 Day | 10 | 10 | 10 | 10 | 10 | 10 | |
| 7 Day | 10 | 10 | 10 | 10 | 10 | 10 | |
| Lethality (%) | 0 | 0 | 0 | 0 | 0 | 0 | |

Since the sample of the galenic composition of the present invention is of a high viscosity, it is difficult to administer orally in an amount greater than 8 g per kg of body weight. At the possible maximum oral dose, all female and male mice survived and any remarkable clinical sign is not observed. The visible anatomical conditions are normal.

Although this invention has been described in its preferred form with a certain degree of particularity, it is appreciated by those skilled in the art that the present disclosure of the preferred form has been made only by way of example and that numerous changes in the details of the construction, combination and arrangement of parts may be resorted to without departing from the spirit and scope of the invention.

What is claimed is:

1. A galenic composition for decreasing blood alcohol concentration comprising an amount of fructose and an aqueous extract of pueraria flower, phaseoli radiati semen and pinelliae tuber sufficient to increase, in vivo, metabolic activity of alcohol dehydrogenase and aldehyde dehydrogenase enzymes and a pharmaceutically acceptable carrier, adjuvant or excipient therefor, wherein said pueraria flower, phaseoli radiati semen, pinelliae tuber and fructose are present in a dry weight ratio of 0.2–1:0.2–1:0.2–1:0.2–1, respectively.

2. The galenic composition of claim 1 wherein said aqueous extract of pueraria flower, phaseoli radiati semen and pinelliae tuber is lyophilized.

3. The galenic composition according to claim 1 further including one or more adjuvant components selected from the group consisting of: arthemisiae herba, alismatis rhizoma, gardeniae fructus, scutellariae radix, coptidis rhizoma, moutan cortex radicis, black soybean, ginseng radix, small red bean, puerariae radix, magnoliae cortex, aurantii nobilis pericarpium, amomi semen, crataegi fructus, arecae semen, massa medicata fermentata, malt, amomi fructus and glycyrrhizae radix.

4. The galenic composition according to claim 3, wherein said pueraria flower, said phaseoli radiati semen, said pinelliae tuber and said fructose are present relative to said adjuvant component in a ratio of 1:0.1–1:1, respectively by dry weight.

5. The galenic composition according to claim 1, further including one or more sweetening agents selected from the group consisting of: dextrose, saccharin, sodium saccharin, sorbitol, white sugar, sugar, lactose, honey, glucose, aspartame and mannitol.

6. The galenic composition according to claim 1, further including one or more flavoring agents selected from the group consisting of: peppermint, spearmint and menthol.

7. The galenic composition according to claim 1 wherein the composition is suitable for oral administration.

8. A galenic composition for decreasing blood alcohol concentration comprising 10 grams of fructose in an aqueous filtered extract of about 7.5 grams of pueraria flower, 7.5 grams of phaseoli radiati semen, 4.5 grams of pinelliae tuber, 3.75 grams of arthemisiae herba, 3.75 grams of gardeniae fructus, 3.75 grams of scutellariae radix, 3.75 grams of coptidis rhizoma, 3.75 grams of black soybean, 3.75 grams of puerariae radix, 3.75 grams of aurantii nobilis pericarpium, 3.75 grams of glycyrrhizae radix and 3.75 grams of ginseng radix to increase metabolic activity of alcohol dehydrogenase and aldehyde dehydrogenase enzymes and a pharmaceutically acceptable carrier, adjuvant or excipient therefor.

9. A method for decreasing blood ethanol concentration comprising administering to a person prior to ethanol ingestion an amount of a composition comprising fructose and an aqueous extract of pueraria flower, phaseoli radiati semen and pinelliae tuber sufficient to increase the metabolic activity of alcohol dehydrogenase and aldehyde dehydrogenase enzymes in the liver of said person administered said composition prior to ingesting alcohol, wherein said pueraria flower, phaseoli radiati semen, pinelliae tuber and fructose are present in a dry weight ratio of 0.2-1:0.2-1:0.2-1:0.2-1, respectively.

10. The method of claim 9 wherein said composition is administered to the person about 30 minutes prior to the ingestion of alcohol.

11. The method of claim 9 wherein the composition is orally administered.

12. The method of claim 9 wherein the amount of said composition administered is prepared by combining 7.5 grams of pueraria flower, 7.5 grams of phaseoli radiati semen and 3.75 grams of pinelliae tuber, adding 150 ml of water and extracting by heating at 80 to 100 degrees centigrade for 2.5 hours, filtering and adding 7.0 grams of fructose to the filtrate.

13. A method of treating alcoholic aftereffects in a mammal about to ingest excessive alcohol by administrating prior to alcoholic ingestion an amount of a composition comprising fructose and an aqueous extract of pueraria flower, phaseoli radiati semen and pinelliae tuber sufficient to increase the metabolic activity of alcohol dehydrogenase and aldehyde dehydrogenase enzymes in the liver of the mammal administered the composition prior to ingesting alcohol, wherein the amount of the composition is 10 to 15 in a lyophilized powder form and said pueraria flower, phaseoli radiati semen, pinelliae tuber and fructose are present in a dry weight ratio of 0.2-1:0.2-1:0.2-1:0.2-1, respectively.

* * * * *